United States Patent [19]

Sheridan

[11] Patent Number: 5,207,655
[45] Date of Patent: May 4, 1993

[54] MEDICO-SURGICAL TUBE INCLUDING IMPROVED MEANS FOR ADMINISTERING LIQUID OR GAS TREATMENT

[75] Inventor: David S. Sheridan, Argyle, N.Y.

[73] Assignee: Sheridan Catheter Corp., Argyle, N.Y.

[21] Appl. No.: 700,411

[22] Filed: May 15, 1991

[51] Int. Cl.⁵ ............................................. A61M 25/00
[52] U.S. Cl. ...................................... 604/247; 604/30; 604/96; 604/280
[58] Field of Search .................... 604/9, 30, 96, 247, 604/256, 264, 278, 280

[56] References Cited

U.S. PATENT DOCUMENTS

| | | |
|---|---|---|
| 3,981,299 | 9/1976 | Murray . |
| 4,657,536 | 4/1987 | Dorman .............................. 604/247 |
| 4,717,379 | 1/1988 | Ekholmer ............................. 604/43 |
| 4,995,863 | 2/1991 | Nichols et al. ...................... 604/247 |
| 5,004,455 | 4/1991 | Greenwood et al. ................. 604/43 |
| 5,030,210 | 7/1991 | Alchas ................................ 604/247 |
| 5,147,334 | 9/1992 | Moss .................................. 604/264 |

Primary Examiner—C. Fred Rosenbaum
Assistant Examiner—C. Maglione
Attorney, Agent, or Firm—Burns, Doane, Swecker & Mathis

[57] ABSTRACT

A medical-surgical tube having a major lumen defined by an inner periphery of a wall of the tube, an injection lumen within the wall of the tube, and at least one one-way valve in the wall. The valve allows fluid to flow from the injection lumen through an outer or inner periphery of the wall of the tube and prevents return of the fluid back into the injection lumen. The tube can include a plurality of spaced-apart valves. The valve can be a piercing in the wall of the tube which is defined by opposed surfaces resiliently biased against each other and extending from the injection lumen to the outer or inner periphery of the wall of the tube.

22 Claims, 2 Drawing Sheets

MEDICO-SURGICAL TUBE INCLUDING IMPROVED MEANS FOR ADMINISTERING LIQUID OR GAS TREATMENT

FIELD OF THE INVENTION

The present invention relates to an improvement in medico-surgical tubes such as endotracheal tubes and in particular, to an economical and uncomplicated means for administering gas or liquid treatment to a selected site in a body passage, vessel, lumen, etc.

BACKGROUND OF THE INVENTION

Various types of medico-surgical tubes employing means for administering medication to a selected site in a body are known in the art. For instance, such tubes include catheters and endotracheal tubes.

A catheter having means for administering liquid medicaments or other preparations is disclosed in U.S. Pat. No. 3,593,713 ("Bogoff"). Bogoff discloses a catheter having a tube surrounded by a tubular jacket which includes a perforated or foraminous area through which a fluid, such as a liquid medicament including antibiotics and anesthetic, can be dispersed within and along the walls of a body orifice, cavity or opening in which the catheter is inserted at the time.

U.S. Pat. No. 3,981,299 ("Murray") discloses a urethral catheter which includes a thin outer membrane provided with a plurality of pores or openings for permitting injections of antibiotics, medication, anesthetics or simple irrigation of the urethral passage.

U.S. Pat. No. 4,186,745 ("Lewis") discloses a catheter having conducting passages within a micropore structure for controlled release of substances such as distilled water, antiseptics, antibiotics, enzymes and other substances.

An endotracheal tube having means for introducing medicinal fluids into the trachea is disclosed in U.S. Pat. No. 4,305,392 ("Chester"). Chester discloses an endotracheal tube having a cylindrical wall, a main lumen defined by an inner surface of the wall, a first secondary lumen within the wall for inflation of a balloon cuff and a second secondary lumen within the wall in fluid communication with a suction chamber having four ports equally spaced about the periphery of the chamber. The ports of Chester's tube are ovoid in shape and are used for introducing anesthesia or irrigation fluid into the trachea or for providing suction without grabbing or invaginating the tracheal mucosa such as for removal of blood clots and other secretions.

U.S. Pat. No. 4,327,721 ("Goldin") discloses a medical device such as an endotracheal tube provided with an annular chamber surrounding an insertion tube wall. A plurality of fenestrations or openings are provided in the chamber and are appropriately shaped so as to atomize a fluid being delivered under pressure thereto through a secondary lumen. The openings in Goldin's tube are used for administering topically active medications, such as local anesthesia, to the tracheal wall and for aspirating any mucous which accumulates above an inflated cuff of the tube.

U.S. Pat. Nos. 4,549,879; 4,671,796; and 4,701,166 ("Groshong") disclose a catheter which includes a closed end and a fluid opening formed by a single linearly extending slit through the tubing wall. The slit forms a two-way valve which remains closed under normal physiologic pressures but is intended to open upon application of predetermined pressure differentials to allow fluid to flow out or be drawn into the catheter. The slit is made by providing a cut through the catheter wall in a direction parallel to the axis of the catheter. The differential pressure required to open the slit is adjusted by changing the slit length.

U.S. Pat. No. 4,693,242 ("Burns") discloses a flexible, non-collapsible conduit system separable but positioned around a standard cuffed, endotracheal tube to allow for direct topical application of medicinal substances to tissues of the larynx and trachea. The tube of Burns includes a secondary lumen in the tube wall which opens into a non-collapsible conduit ring fixed around a proximal end of the inflatable cuff and outer perforations in the conduit ring leak topical anesthetic or other medicinal fluid to the adjacent upper tracheolaryngeal areas. Additional conduits having outer perforations or openings are connected to the conduit for leaking topical anesthetic or other medicinal fluid to adjacent lower tracheal or bronchial area. The perforations of Burns are elliptical in shape as viewed along the outer periphery of the conduits and are formed by tapered openings which become wider in a direction towards the outer periphery of the conduits, the conduit system maintaining fluid communication regardless of the manipulation of the tube or cuff.

In general, an endotracheal tube is a plastic or rubber, most commonly PVC, tube used for securing the airway of critically ill or anesthetized patients. Such a tube is necessary in order to perform mechanical positive pressure ventilation of the lungs and to prevent the possibility of aspiration or airway obstruction.

The larynx and trachea, through which this tube must pass, are amongst the most sensitive areas of the body. The presence of a tube in these structures invokes powerful reflexes of pain, coughing, gagging, retching and vomiting. It is advantageous to administer a local anesthetic containing solution to the larynx and trachea on initial placement of the tube and subsequently as required while the tube is still in place. This prevents the pain, discomfort and potentially dangerous fits of coughing that might be produced by the presence of the tube in the larynx and trachea. Removing the tube to administer local anesthetic is time consuming, difficult and occasionally dangerous. An endotracheal tube is disclosed in commonly owned U.S. Pat. No. 4,977,894, issued on Dec. 18, 1990, which matured from Ser. No. 07/334,435 filed on Apr. 7, 1989, a continuation of Ser. No. 07/031,877 filed on Mar. 30, 1987, the disclosure of which is hereby incorporated by reference. The endotracheal tube includes means for administering local anesthetic to the sensitive laryngo-tracheal area through the wall of the endotracheal tube. In particular, several small openings in fluid communication with an injection lumen in the wall of the tube are provided on the anterior aspect of the distal 11 cm of the tube corresponding to the anatomical position of the epiglottis, larynx and trachea.

SUMMARY OF THE INVENTION

An object of the present invention is to provide a medical-surgical tube comprising a tube having a major lumen defined by an inner periphery of a wall of the tube, an injection lumen within the wall of the tube and at least one one-way valve means in the wall for allowing fluid to flow from the injection lumen through the wall of the tube, the valve means substantially preventing return of the fluid, such as liquid or gas, through the wall back into the injection lumen. A check valve or other means can be provided to prevent return of fluid through the proximal end of the injection lumen tail. The tube can comprise a tracheal tube, thoracic or trocar catheter or other medical-surgical tube.

According to the invention, the valve means can comprise a plurality of valve means, each of the valve means being spaced from an adjacent one of the valve means along the injection lumen. In particular, the valve means can comprise a piercing in the wall of the tube, the piercing being defined by opposed surfaces resiliently biased against each other and extending from the injection lumen to the outer or inner periphery of the wall of the tube. The opposed surfaces can extend rectilinearly and can be in contact with each other when the valve is closed. The surfaces form a gap therebetween when the valve is open to allow passage of the fluid from the injection lumen, through the gap and outwardly of the outer or inner periphery of the tube. The piercings can extend along axes which are parallel to each other and can be inclined with respect to a direction of flow of fluid passing through the injection lumen at an angle other than 90°. The angle can be less than 45°. For instance, the angle can be less than 30° such as about 22°.

According to one embodiment of the invention, the valve means causes fluid under pressure in the injection lumen to be sprayed outwardly of the outer periphery of the tube as an atomized spray. In particular, where the valve means comprises a piercing in the wall of the tube, depending on the size of the piercing and amount of fluid pressure, an atomized spray of fluid can be ejected from the piercing. Alternatively, the piercing can be sized to provide a coarse spray or liquid stream of fluid under pressure in the injection lumen. The piercing preferably has a maximum dimension in a direction perpendicular or at an angle to the direction of flow of fluid through the piercing of no greater than the diameter of the injection lumen.

According to another embodiment, another lumen may be provided in the wall of the tube and a balloon cuff may be provided on the outer periphery of the tube, this lumen being in fluid communication with the balloon cuff for inflating and deflating the balloon cuff. Other lumens may also be provided within the wall of the tube for other applications. The tube can be of soft plastic having a durometer hardness in the range of 40 to 100 Shore A. Where the valve means comprises a piercing, the piercing can have a maximum dimension in a direction perpendicular or at an angle to the direction of flow of the fluid through the piercing, the dimension being selected as a function of the softness of the plastic tube and the thickness of the wall of the tube measured between the injection lumen and outer or inner periphery of the tube depending on whether the piercings open exteriorily of the tube or open into the central lumen.

The piercing can be formed by opposed surfaces having various configurations. For instance, the opposed surfaces can be more narrow at a portion thereof adjacent the outer or inner periphery of the tube than at a portion thereof adjacent the injection lumen. Alternatively, the opposed surfaces can be more narrow adjacent the injection lumen than at the outer or inner periphery of the tube. The opposed surfaces can also be substantially constant in dimension along the length thereof.

BRIEF DESCRIPTION OF THE DRAWINGS

The invention is described with reference to the accompanying drawings, in which:

FIG. 2 is a top perspective view of a portion of the tube shown in FIG. 1a.

DETAILED DESCRIPTION OF THE PREFERRED EMBODIMENTS

Figure 1:
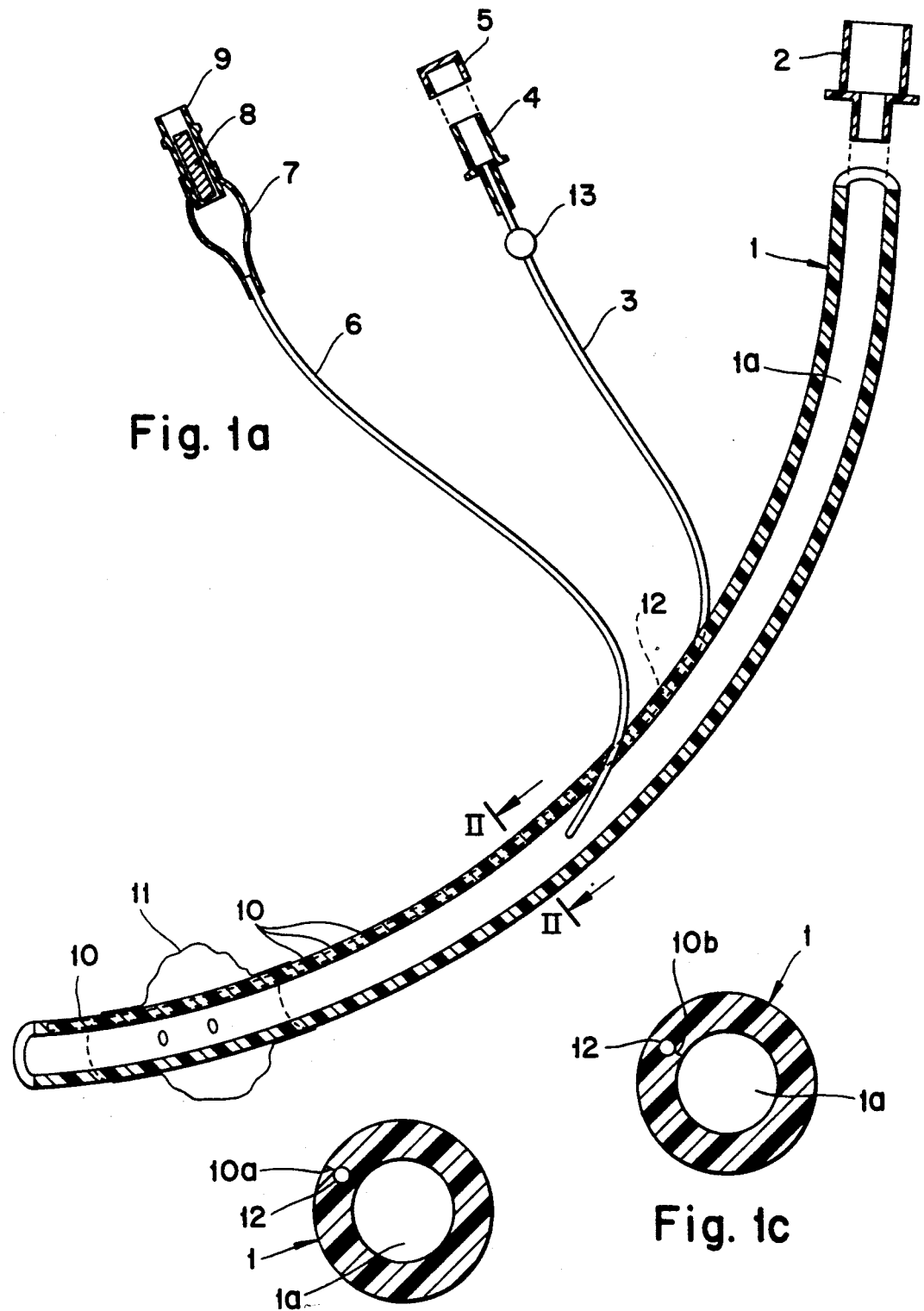
FIG. 1a is a cross-sectional view of a medicosurgical tube having one-way valve means in accordance with the invention.
FIG. 1b shows a cross-section of the tube shown in FIG. 1a taken along line II—II wherein the one-way valve ejects fluid through the outer periphery of the tube.
FIG. 1c shows a cross-section of the tube according to the invention wherein the one-way valve opens into a central lumen.

The invention provides an administering means which can be used in connection with a variety of medico-surgical tubes, especially endotracheal tubes. A laryngo-tracheal analgesia endotracheal tube has the built-in capability of topically anesthetizing the sensitive structures of the epiglottis, larynx and trachea when the tube is in place. The tube incorporates an injection lumen, for the purpose of drug administration, in the anterior aspect of the wall of the endotracheal tube. Local anesthetic injected through the injection lumen is deposited on and around the epiglottis, larynx and trachea. The advantage of topically anesthetizing these areas is that potentially dangerous reflexes of coughing, laryngospasm, hypertension and tachycardia can be prevented thereby facilitating safer anesthesia and patient management when endotracheal intubation is required.

A medico-surgical tube in accordance with the invention is shown in FIGS. 1-4. In particular, FIG. 1a shows a tube 1 (which in the embodiment shown comprises a tracheal tube) having a connector 2 at a proximal end thereof. The tube 1 includes a major or central lumen 1a defined by an inner surface of the tube wall.

The medico-surgical tube includes at least one injection lumen and possibly one or more secondary lumens. For instance, as shown in FIG. 1a, one end of an injection tail 3 is inserted within an injection lumen 12 in the tube 1. The injection tail 3 has an injection connector 4 at the opposite end thereof and an injection cap 5 is provided for sealing the injection connector 4. A sealing means 13, such as a check valve, can be provided at the proximal end of the injection tail 3.

The medico-surgical tube can include a balloon cuff. For instance, one end of a cuff inflation tail 6 can be inserted in a secondary lumen or it can extend along the outer periphery of the tube wall, as shown in FIG. 1a. An opposite end of the inflation tail 6 includes a pilot balloon 7, a valve such as a one-way valve 8 in fluid communication with the balloon 7 and a luer end 9 of the one-way valve 8. The inflation tail 6 is in fluid communication with a balloon cuff 11 provided around the tube 1.

The tube 1 includes one-way valve means 10 provided in the tube wall so as to be in fluid communication with the injection lumen 12. The valve means 10 can comprise a plurality of spaced-apart pierced portions of the tube. Such piercings 10 should allow fluid to pass outwardly of the tube wall when the fluid is pressurized in the injection lumen 12 such as by means of a syringe. Depending on the type of fluid discharge desired, e.g. atomized spray, coarse spray, liquid stream, etc., it will be necessary to select an appropriate width/diameter/length of the piercing. In addition, the softness of the tube material and thickness between the injection lumen and outer/inner periphery of the tube can be varied to provide the desired type of fluid discharge.

As shown in FIG. 1b, the piercings 10a can extend between the injection lumen 12 and the outer periphery of the tube. Alternatively, the piercings 10b can extend between the injection lumen 12 and the central lumen 1a, as shown in FIG. 1c.

Figure 2:
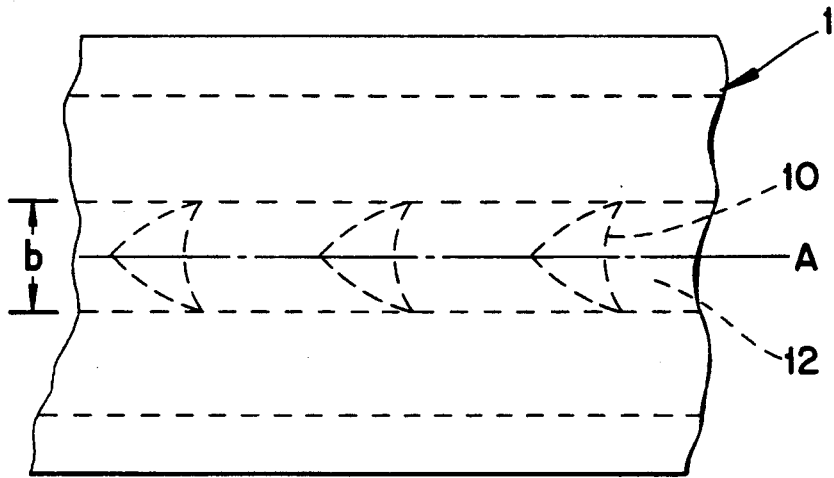
Figure 3:
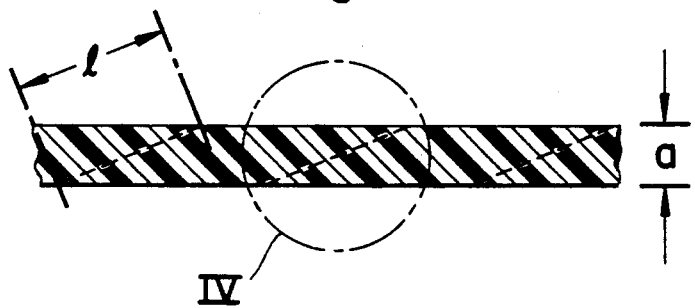
FIG. 3 is a side cross-sectional view of the portion of the tube shown in FIG. 2.
Figure 4:
FIG. 4 is an enlargement of the detail IV shown in FIG. 3.

As shown in FIG. 2, each of the piercings 10 can lie in a plane passing through a central axis A of the tube. Also, the piercings 10 can be inclined so as to face upstream or downstream with respect to the direction of flow of the fluid in the injection lumen 12 and/or they can be inclined in a radial or circumferential direction with respect to the central axis A of the tube. For ease of fabrication, however, it is preferred that the piercings have axes which are generally parallel to each other and inclined in a direction facing downstream with respect to the direction of flow in the injection lumen 12, as shown in FIG. 3. For instance, the piercings can be inclined at an angle other than 90° with respect to the direction of flow of fluid passing through the injection lumen. This angle can be less than 45°, such as about 22°, for example, as shown in FIG. 4.

The tube 1 has a wall thickness "a" between the injection lumen 12 and the outer/inner periphery of the tube 1, as shown in FIG. 3. The thickness "a" can be about 0.015 inch, for instance. The injection lumen 12 has a diameter "b" as shown in FIG. 2. In the preferred embodiment, the piercings 10 have a maximum dimension, i.e. width, of no greater than the diameter "b". The length "l" of the piercings 10 is greater than the distance "a" when the piercings 10 are inclined as shown in FIG. 3. For instance, this length "l" can be about 3 times "a".

Each of the piercings is defined by a pair of opposed surfaces resiliently biased against each other. The opposed surfaces can extend rectilinearly and are in contact with each other when the valve is closed. The opposed surfaces form a gap therebetween when the valve is open to allow passage of fluid from the injection lumen, through the gap and outwardly of the outer or inner periphery of the tube.

The piercings 10 can be formed by projecting a piercer such as a needle or wire into the outer periphery or inner periphery of the tube, or passing the piercer along the injection lumen 12 and through the tube wall or combinations thereof. All of the piercings in a particular tube should either open outwardly of the outer periphery of the tube or into the central lumen.

To form piercings which open exteriorily of the tube, the piercer can be inserted into the injection lumen 12 along the axis thereof, then (with the tube in a slightly bent configuration) the point of the piercer can be pushed through the portion of the tube wall located between the injection lumen 12 and the outer periphery of the tube 1 to form piercing 10a, as shown in FIG. 1b. Alternatively, the piercer can be pushed into the outer periphery of the tube 10, through the tube wall and into the injection lumen 12.

To form piercings which open inwardly into the central lumen, the piercer can be pushed from the central lumen 1a into the inner periphery of the tube, through the tube wall and into the injection lumen 12 to form piercing 10b, as shown in FIG. 1c. Alternatively, the piercer can be passed along the injection lumen 12, through the tube wall and into the central lumen 1a.

If the piercer comprises a needle having a tapered point, the tapered point can be pushed partially or entirely through the tube wall to form the piercings 10. If the tapered point is pushed partially through the tube wall, the opposed surfaces forming the piercing will be tapered along the length thereof so as to be more narrow at either the outer periphery of the tube, the inner periphery of the tube or at the injection lumen. In this way, no drilling of the tube is required which would be undesirable in that the drilled holes would remain open. Furthermore, inaccurate drilling could result in undesirable fluid connections between the injection lumen and the central lumen.

In order to provide a self-sealing piercing, the needle should have a thin diameter with or without a tapered point. For instance, the needle can have a diameter of 0.025 inch. Larger needle diameters will allow a larger stream of liquid to be ejected from the piercing. When making a plurality of piercings, after a particular piercing is made, the needle can be backed up in the injection lumen about one-half an inch, the tube can be advanced and bent (if not already bent) and the needle can again be pushed forward to form another piercing. It has been found that a Singer needle of a 3-9 Darners is suitable for forming the piercings. Alternatively, a thin wire such as piano wire could be used to form the piercings.

While the invention has been described with reference to the foregoing embodiments, various changes and modifications may be made thereto which fall within the scope of the appended claims.

What is claimed is:

1. A medical-surgical tube comprising:
   a tube having a major lumen defined by an inner periphery of a wall of the tube;
   an injection lumen within the wall of the tube; and
   at least one one-way valve means in the wall for allowing fluid to flow from the injection lumen in one direction through the wall of the tube, the valve means preventing the passage of fluid in an opposite direction through the wall and back into the injection lumen, the valve means comprising a piercing in the wall of the tube, the piercing being inclined at an angle other than 90° with respect to a direction of flow of fluid passing through the injection lumen.

2. The tube of claim 1, further comprising an injection tail in fluid communication with the injection lumen, the injection tail including a check valve or other means to prevent return of fluid through a proximal end of the injection tail.

3. The tube of claim 1, wherein the at least one valve means comprises a plurality of said valve means, each of said valve means being spaced from an adjacent one of said valve means along said injection lumen.

4. The tube of claim 3, wherein the piercing is defined by opposed surfaces resiliently biased against each other and extending from the injection lumen to the outer periphery of the wall of the tube.

5. The tube of claim 4, wherein the injection lumen lies in a plane passing through a central axis of the tube.

6. The tube of claim 5, wherein the angle is less than 45°.

7. The tube of claim 5, wherein the angle is less than 30°.

8. The tube of claim 5, wherein the angle is about 22°.

9. The tube of claim 1, wherein the piercing is defined by opposed surfaces resiliently biased against each other and extending from the injection lumen to the outer periphery of the wall of the tube.

10. The tube of claim 9, wherein the opposed surfaces extend rectilinearly and are in contact with each other when the valve is closed, the surfaces forming a gap therebetween when the valve is open to allow passage of the fluid from the injection lumen, through the gap and outwardly of the outer periphery of the tube.

11. The tube of claim 9, wherein said opposed surfaces are inclined at an angle of less than 45° to a direction of flow of fluid passing through the injection lumen.

12. The tube of claim 1, wherein said valve means causes fluid under pressure in the injection lumen to be sprayed outwardly of the outer periphery of the tube as an atomized spray.

13. The tube of claim 1, wherein the piercing is sized to provide an atomized spray of fluid under pressure in the injection lumen.

14. The tube of claim 1, wherein the piercing is sized to provide a coarse spray of fluid under pressure in the injection lumen.

15. The tube of claim 1, wherein the valve means comprises a piercing in the wall of the tube, the piercing being sized to provide a liquid stream of fluid under pressure in the injection lumen.

16. The tube of claim 1, wherein the piercing is sized to provide a liquid stream of fluid under pressure in the injection lumen.

17. The tube of claim 1, further comprising a secondary lumen in the wall of the tube and a balloon cuff on the outer periphery of the tube, the secondary lumen being in fluid communication with the balloon cuff for inflating and deflating the balloon cuff.

18. The tube of claim 1, wherein the tube is of soft plastic having a durometer hardness in the range of 40 to 100 Shore A.

19. The tube of claim 1, wherein the tube comprises a tracheal tube.

20. The tube of claim 1, wherein the tube comprises a thoracic or trocar catheter.

21. The tube of claim 1, wherein the tube is of flexible plastic, the piercing being expandable to a width by pressurized fluid passing through the piercing, the width being selected as a function of durometer of the plastic tube, the thickness of the wall of the tube measured between the inner and outer peripheries of the tube, and the shape and size of a piercing device used to form the piercing.

22. The tube of claim 1, wherein the piercing is formed by opposed surfaces which are more narrow at a portion thereof adjacent the outer periphery of the tube than at a portion thereof adjacent the injection lumen.

* * * * *